(12) United States Patent
Solomon et al.

(10) Patent No.: US 10,912,896 B2
(45) Date of Patent: Feb. 9, 2021

(54) ENHANCED INFUSION-SITE PAIN-REDUCTION FOR DRUG-DELIVERY DEVICES

(71) Applicant: SteadyMed Ltd., Rehovot (IL)

(72) Inventors: Ian Solomon, Jerusalem (IL); Jacob Rand, Herzliya (IL); Jonathan Rigby, San Ramon, CA (US)

(73) Assignee: STEADYMED LTD., Tel Aviv (IL)

( * ) Notice: Subject to any disclaimer, the term of this patent is extended or adjusted under 35 U.S.C. 154(b) by 0 days.

(21) Appl. No.: 16/126,036

(22) Filed: Sep. 10, 2018

(65) Prior Publication Data

US 2019/0001076 A1 Jan. 3, 2019

Related U.S. Application Data

(63) Continuation of application No. 14/384,131, filed as application No. PCT/IL2013/050223 on Mar. 11, 2013, now Pat. No. 10,071,209.

(Continued)

(51) Int. Cl.
*A61M 5/142* (2006.01)
*A61M 5/42* (2006.01)
(Continued)

(52) U.S. Cl.
CPC ........... *A61M 5/422* (2013.01); *A61N 1/0456* (2013.01); *A61N 1/0476* (2013.01);
(Continued)

(58) Field of Classification Search
CPC .............. A61M 5/422; A61M 5/14248; A61M 5/14276; A61M 2005/3022; A61N 1/0456;
(Continued)

(56) References Cited

U.S. PATENT DOCUMENTS

| 4,842,598 A | 6/1989 | Tran |
| 4,843,598 A | 6/1989 | Medlin |

(Continued)

FOREIGN PATENT DOCUMENTS

| CA | 2812877 A1 | 4/2012 |
| DE | 3621846 A1 | 1/1988 |

(Continued)

OTHER PUBLICATIONS

Lee et al., "Battery Dimensional Changes Occuring During Charge/Discharge Cycles—Thin Rectangular Lithium Ion and Polymer Cells," Journal of Power Sources, 119-121: 833-837 (2003).

(Continued)

*Primary Examiner* — Tiffany Legette
(74) *Attorney, Agent, or Firm* — Kilpatrick Townsend & Stockton LLP

(57) ABSTRACT

The present invention provides an infusion-patch comprising; a cannula; a base; at least one adhesive region in said base suitable for skin attachment; at least one skin-access area within said base; and at least one conduit in fluid connection with said at least one skin access area, wherein said at least one conduit in fluid connection with said at least one skin access area facilitates the transfer of an anesthetic substance within at least a first anesthetic-reservoir which may be removably attached and in fluid connection with said at least one contact area, promoting delivery of said anesthetic substance to said at least one skin-access areas, and wherein said anesthetic substance delivered to said skin-access areas may be at least partially replenished without removing said infusion-patch. Embodiments of the present invention include methods of administering a drug using the infusion-patch.

20 Claims, 5 Drawing Sheets

Related U.S. Application Data

(60) Provisional application No. 61/670,128, filed on Jul. 11, 2012, provisional application No. 61/611,015, filed on Mar. 15, 2012.

(51) Int. Cl.
  *A61N 1/36* (2006.01)
  *A61N 1/04* (2006.01)
(52) U.S. Cl.
  CPC ....... *A61N 1/0492* (2013.01); *A61N 1/36021* (2013.01); *A61M 5/14248* (2013.01)
(58) Field of Classification Search
  CPC . A61N 1/0476; A61N 1/0492; A61N 1/36021
  See application file for complete search history.

(56) References Cited

U.S. PATENT DOCUMENTS

| | | | |
|---|---|---|---|
| 4,886,514 A | 12/1989 | Maget | |
| 5,062,834 A | 11/1991 | Gross et al. | |
| 5,102,389 A | 4/1992 | Hauser | |
| 5,108,852 A | 4/1992 | Tomantschger et al. | |
| 5,109,850 A | 5/1992 | Blanco et al. | |
| 5,134,046 A | 7/1992 | Chow et al. | |
| 5,318,557 A | 6/1994 | Gross | |
| 5,354,264 A | 10/1994 | Bae et al. | |
| 5,389,070 A * | 2/1995 | Morell ................. | A61M 5/204 604/183 |
| 5,436,372 A | 7/1995 | Yoshida et al. | |
| 5,438,249 A | 8/1995 | Chang et al. | |
| 5,505,706 A | 4/1996 | Maus et al. | |
| 5,527,288 A | 6/1996 | Gross et al. | |
| 5,563,004 A | 10/1996 | Buzzelli et al. | |
| 5,643,207 A | 7/1997 | Rise | |
| 5,677,083 A | 10/1997 | Tomiyama | |
| 5,814,020 A | 9/1998 | Gross | |
| 5,827,233 A | 10/1998 | Futagawa et al. | |
| 5,848,991 A | 12/1998 | Gross et al. | |
| 5,938,640 A | 8/1999 | Maget et al. | |
| 5,980,741 A | 11/1999 | Schnell et al. | |
| 6,150,053 A | 11/2000 | Murata et al. | |
| 6,186,982 B1 | 2/2001 | Gross et al. | |
| 6,296,967 B1 | 10/2001 | Jacobs et al. | |
| 6,312,409 B1 | 11/2001 | Gross | |
| 6,322,532 B1 | 11/2001 | D'Sa et al. | |
| 6,358,239 B1 | 3/2002 | Rake et al. | |
| 6,377,848 B1 | 4/2002 | Garde et al. | |
| 6,400,489 B1 | 6/2002 | Suzuki et al. | |
| 6,429,189 B1 * | 8/2002 | Borodic ................ | A61K 38/164 514/13.2 |
| 6,465,125 B1 | 10/2002 | Takami et al. | |
| 6,506,520 B1 | 1/2003 | Inoue et al. | |
| 6,534,218 B1 | 3/2003 | Okada et al. | |
| 6,537,249 B2 | 3/2003 | Kriesell et al. | |
| 6,537,250 B1 | 3/2003 | Kriesel | |
| 6,577,039 B2 | 6/2003 | Ishida et al. | |
| 6,589,229 B1 | 7/2003 | Connelly et al. | |
| 6,733,485 B1 | 5/2004 | Whitehurst et al. | |
| 6,982,514 B1 | 1/2006 | Lu et al. | |
| 7,242,134 B2 | 7/2007 | Wallace et al. | |
| 7,364,568 B2 | 4/2008 | Angel et al. | |
| 7,541,715 B2 | 6/2009 | Chiang et al. | |
| 8,834,454 B2 | 9/2014 | Genosar et al. | |
| 9,011,376 B2 | 4/2015 | Goldstein | |
| 10,071,209 B2 | 9/2018 | Solomon et al. | |
| 2002/0107480 A1 | 8/2002 | Kriesel et al. | |
| 2002/0156461 A1 | 10/2002 | Joshi | |
| 2002/0169439 A1 | 11/2002 | Flaherty | |
| 2003/0014014 A1 | 1/2003 | Nitzan | |
| 2003/0205582 A1 | 11/2003 | Joshi et al. | |
| 2004/0059282 A1 | 3/2004 | Flock et al. | |
| 2004/0068224 A1 | 4/2004 | Couvillon et al. | |
| 2004/0115068 A1 | 6/2004 | Hansen et al. | |
| 2004/0115523 A1 | 6/2004 | Hommura et al. | |
| 2004/0115530 A1 | 6/2004 | Maeda et al. | |
| 2004/0138612 A1 | 7/2004 | Shermer et al. | |
| 2005/0096587 A1 | 5/2005 | Santini et al. | |
| 2006/0052768 A1 | 3/2006 | Joshi et al. | |
| 2006/0069344 A1 | 3/2006 | Southam et al. | |
| 2006/0102455 A1 | 5/2006 | Chiang et al. | |
| 2006/0106346 A1 | 5/2006 | Sullivan et al. | |
| 2006/0200073 A1 | 9/2006 | Radmer et al. | |
| 2007/0055179 A1 * | 3/2007 | Deem ............... | A61M 37/0092 601/2 |
| 2008/0188779 A1 | 8/2008 | Vellero | |
| 2008/0281270 A1 | 11/2008 | Cross et al. | |
| 2009/0018424 A1 * | 1/2009 | Kamath ................ | A61B 5/412 600/347 |
| 2009/0069746 A1 | 3/2009 | Miller et al. | |
| 2009/0093772 A1 | 4/2009 | Genosar et al. | |
| 2009/0312706 A1 * | 12/2009 | Shantha ................ | A61M 5/427 604/112 |
| 2010/0022992 A1 | 1/2010 | Genosar et al. | |
| 2010/0056874 A1 | 3/2010 | Dijksman et al. | |
| 2010/0106088 A1 | 4/2010 | Yodfat et al. | |
| 2010/0130931 A1 | 5/2010 | Yodfat et al. | |
| 2010/0152658 A1 | 6/2010 | Hanson et al. | |
| 2010/0266638 A1 | 10/2010 | Turkel et al. | |
| 2010/0274221 A1 | 10/2010 | Sigg et al. | |
| 2011/0098652 A1 | 4/2011 | Haster et al. | |
| 2011/0160655 A1 | 6/2011 | Hanson et al. | |
| 2011/0166543 A1 * | 7/2011 | Stepovich ............ | A61J 1/2096 604/413 |
| 2011/0306929 A1 | 12/2011 | Levesque et al. | |
| 2011/0313391 A1 | 12/2011 | Knapp, II et al. | |
| 2012/0041338 A1 | 2/2012 | Chickering, III | |
| 2012/0042517 A1 | 2/2012 | Tronnes et al. | |
| 2012/0238849 A1 | 9/2012 | Holtzclaw et al. | |
| 2014/0148761 A1 | 5/2014 | Rotem et al. | |
| 2014/0163339 A1 | 6/2014 | Goldstein et al. | |
| 2014/0171867 A1 | 6/2014 | Walsh et al. | |
| 2015/0017493 A1 | 1/2015 | Genosar et al. | |
| 2015/0038907 A1 | 2/2015 | Rotem | |
| 2016/0361491 A1 | 12/2016 | Shaked et al. | |
| 2017/0304532 A1 | 10/2017 | Rotem | |
| 2018/0035935 A1 | 2/2018 | Goldstein et al. | |

FOREIGN PATENT DOCUMENTS

| | | |
|---|---|---|
| DE | 19809483 A1 | 9/1999 |
| EP | 0676214 A1 | 10/1995 |
| EP | 1912690 A1 | 4/2008 |
| EP | 2621558 A1 | 8/2013 |
| EP | 2825225 A1 | 1/2015 |
| EP | 2827923 A1 | 1/2015 |
| GB | 2221394 A1 | 2/1990 |
| IL | 169807 | 2/2006 |
| JP | 02-131376 A | 5/1990 |
| JP | 04-127885 A | 4/1992 |
| WO | 97/010012 A1 | 3/1997 |
| WO | 2001/021234 A1 | 3/2001 |
| WO | 01/51108 A1 | 7/2001 |
| WO | 2002/069935 A1 | 9/2002 |
| WO | 2004/067066 A1 | 2/2003 |
| WO | 2004/006982 A2 | 1/2004 |
| WO | 2005/124918 A2 | 12/2005 |
| WO | 2007/010522 A1 | 1/2007 |
| WO | 2007/129317 A1 | 11/2007 |
| WO | 2008/062335 A1 | 5/2008 |
| WO | 2008/122983 A1 | 10/2008 |
| WO | 2011/075100 A1 | 6/2011 |
| WO | 2012/042517 A1 | 4/2012 |
| WO | 2013/136327 A1 | 9/2013 |
| WO | 2013/140395 A1 | 9/2013 |

OTHER PUBLICATIONS

Ginsberg, Barry H., MD, PhD, "Patch Pumps for Insulin," *Journal of Diabetes Science and Technology* 2019, vol. 13(I) pp. 27-33.

(56) References Cited

OTHER PUBLICATIONS

Heinemann, et al., "Patch Pumps: Are They All the Same?" *Journal of Diabetes Science and Technology* 2019, vol. 13(I) pp. 34-40.

* cited by examiner

ENHANCED INFUSION-SITE PAIN-REDUCTION FOR DRUG-DELIVERY DEVICES

CROSS-REFERENCES TO RELATED APPLICATIONS

This application is a continuation of U.S. patent application Ser. No. 14/384,131, filed Sep. 9, 2014, entitled "ENHANCED INFUSION-SITE PAIN-REDUCTION FOR DRUG-DELIVERY DEVICES," which is a '371 national stage application of PCT International Patent Application No. PCT/IL2013/0050223, filed Mar. 11, 2013, entitled "ENHANCED INFUSION-SITE PAIN-REDUCTION FOR DRUG-DELIVERY DEVICES," which claims the benefit of priority to U.S. Provisional Patent Application No. 61/670,128, filed Jul. 11, 2012, entitled "ENHANCED INFUSION-SITE PAIN-REDUCTION FOR DRUG-DELIVERY DEVICES," and claims the benefit of priority to U.S. Provisional Patent Application No. 61/611,015, filed Mar. 15, 2012, entitled "INFUSION-SITE PAIN-REDUCTION FOR DRUG-DELIVERY DEVICES," the entire contents of which are herein incorporated by reference in their entirety.

FIELD OF THE INVENTION

The present invention is in the field of liquid drug-delivery, in relation to infusible or injectable liquid drug delivered subcutaneously. In particular, the present invention provides a device and method for addressing the problem of pain associated with certain drug-delivery and describes a system for minimizing such pain integrated within the base of a patch such as an infusion set or a patch-pump and a method of use thereof.

BACKGROUND OF THE INVENTION

The pain associated with the insertion of needles or cannulas into the subcutaneous space is well known and can be addressed in a limited fashion by rubbing anesthetic cream into the insertion site prior to introduction of the rigid cannula (needle) or flexible cannula. Additionally, some drugs incite a stinging sensation, inflammatory response, vaso-dilatory response or pain response during injection for at least some of the duration of the injection or infusion.

Examples of drugs whose infusion causes pain at the infusion-site are adalimumab (Abbott Laboratories, Ill., USA) and treprostinil (United Therapeutics Corp., MD, USA). There are three main methods known in the art for reducing pain at the infusion-site during an injection or infusion:

(1) Preparation of the skin directly prior to the injection, whether by using an anesthetic cream, patch or topical spray containing lidocaine, for example LidoCream 4 (Golden Touch LLC, KY, USA). The last named is a cream which is typically rubbed into the skin before application of the infusion set.

(2) Preparation of the infusion site well in advance of the injection, in order to prepare and numb the area. For example, the use of capsaicin-based patches, such as the Qutenza patch (NeurogesX, Inc., CA, USA) has been shown to have a long term effect which increases towards an optimal level over a couple of weeks.

(3) Release of an anesthetic such as lidocaine or bupivacaine from the adhesive layer of an infusion set or patch-pump, as described in US patent application #20110313391.

In approaches (1) and (3), the release of the anesthetic is typically only effective for a few hours, after which time the effect gradually drops off. Thus, when infusing a pain-causing drug for periods significantly longer that this, there is a lack of suitable systems to ensure the continuity or refreshing of the pain-relieving effect.

OBJECT OF THE INVENTION

Thus the objective of the present invention is to a means for an infusion-set or patch-pump having a renewed and/or maintaining an ongoing high-level of pain-reduction treatment of the skin-area being treated, significantly beyond what is currently achievable using the existing approaches.

It is a further object of the invention to enable the patient to determine the onset and or renewal of this pain-reducing effect at his own convenience.

It is yet a further objective of the invention to provide the above functionality while maintaining a compact delivery system, for example, without significantly increasing the size or height of the infusion-set or patch-pump.

BRIEF SUMMARY OF THE INVENTION

The present invention provides a system for filling and replenishing skin-contact areas underneath an infusion-set or patch-pump (hereafter collectively termed an "infusion patch") with a pain-reducing substance, while the patient continues to have said infusion patch adhered to his skin.

Said system provides for an anesthetic or other pain-reducing drug to be delivered from a reservoir to said skin-contact areas, without disturbing the ongoing delivery of the drug from the cannula to the subcutaneous layer.

In some embodiments, this invention provides an infusion-patch comprising:
a cannula
a base;
at least one adhesive region in said base suitable for skin attachment;
at least one skin-access area within said base; and
at least one conduit in fluid connection with said at least one skin access area,
wherein said at least one conduit in fluid connection with said at least one skin access area facilitates the transfer of an anesthetic substance within at least a first anesthetic-reservoir which may be removably attached and in fluid connection with said at least one contact area, promoting delivery of said anesthetic substance to said at least one skin-access areas, and wherein said anesthetic substance delivered to said skin-access areas may be at least partially replenished without removing said infusion-patch.

In some embodiments, the term "cannula" encompasses the device commonly known in the field of medical sciences. In some embodiments, the term "cannula" is to be understood to encompass any tube-like structure that can be inserted into the body. In some embodiments, the term "cannula" refers to a rigid cannula or flexible cannula. In some embodiments a needle is used instead of a cannula. In yet another embodiment a needle array is used.

The infusion-patches of this invention comprise a base through which a cannula inserts. Such cannula may be connected to a drug reservoir, for delivery of a drug product as described herein.

The base of the infusion-patches of this invention will also comprise at least one adhesive region suitable for skin attachment. Such adhesive region may comprise strips of adhesive material which facilitate adhesion of the infusion patches of this invention to the subject being treated. In some embodiments, such adhesive regions may comprise double-sided adhesive materials. In some embodiments, such adhesive material may be any such material known in the art, which are commonly used for adherence to skin. It will be appreciated that any such adhesive material is contemplated for inclusion in the devices and uses of this invention.

In some embodiments, the base further comprises a skin access area. In some embodiments, such skin access area is a channel in the base, which channel comprises apertures located along a length of said channel, which apertures enable release of a pain reducing substance, such as an anesthetic substance for example, contained in a liquid, cream, etc. so that such anesthetic substance delivered to said channel may be released externally from the base, so that it is in contact with the skin area to which such base is applied.

Said pain-reducing substance may, in some embodiments, comprise a local anesthetic, analgesic or anti-inflammatory compound and its contact with the skin following release from said channel reduces pain at the proximally located skin site, which in turn is proximally located to, or also comprises a site of infusion of a second substance delivered thereto. The term "anesthetic substance," in some embodiments, refers to the use of any compound, such as a drug or biomaterial, such as a protein or peptide, which serve to reduce local infusion-site pain.

In some embodiments, such anesthetic substances may include benzocaine, butamben, dibucaine, lidocaine, oxybuprocaine, pramoxine, proparacaine, proxymetacaine, tetracaine and others. In some embodiments, such anesthetic substances may include a neurotoxin, for example a toxin isolated from *Clostridium botulinum*.

In some embodiments, the anesthetic-reservoir can either be detachable from said infusion-patch one, or integrated within the device.

In some embodiments, the infusion-patch further comprises a connector in fluid connection with said cannula, wherein said at least a first anesthetic-reservoir is external to said infusion-patch; and may be attached to said connector via a mechanism that may be removed and optionally replaced with at least a second anesthetic-reservoir.

In some aspects, when the anesthetic reservoir is detachable from the infusion-patches of this invention, such reservoir may be any convenient shape or size. In some embodiments, for example, such anesthetic-reservoir is in the form of a tube containing the anesthetic, analgesic, or anti-inflammatory substance and said tube is connected to said infusion patch via a connector attached to said infusion-patch.

According to this aspect, and in some embodiments, such connector may provide a seal so that delivery of said anesthetic, analgesic, or anti-inflammatory substance from said reservoir to said conduit diminishes or prevents escape of said substance during transfer. In some embodiments, such connector may operate via screw cap or other releasable connection which permits an appropriate seal during delivery of the substance.

According to this aspect, and in some embodiments, such connector may create a liquid connection to the skin-contact areas under said infusion-patch.

In some aspects, when the anesthetic reservoir is integrated within the device, in some embodiments, the reservoir or reservoirs containing an anesthetic, analgesic, or anti-inflammatory substance may be implemented as nodules which come into fluid connection with said skin-contact areas on rupturing of a barrier (such as a weak-weld) between said nodule and said skin-contact areas. In some embodiments, the integrated reservoir containing an anesthetic, analgesic, or anti-inflammatory substance is integrated with an actuator, which drives the patch-pump, such that said actuator drives both the drug delivery and the topical anesthetic delivery simultaneously.

In some embodiments, an infusion set according to the present invention may further comprise a series of transcutaneous electrical nerve stimulation (TENS) electrodes integrated within the skin adhesion side of said set; whereby TENS is used as a further pain-reducing element of the invention.

In some embodiments, the invention provides methods of use of the devices of this invention, providing a means of pain reduction at a site of drug delivery for any drug delivery for which such application would be beneficial.

In some embodiments, the invention provides a method of treating pulmonary arterial hypertension using the infusion-patch as herein described to deliver Treprostinil. In some embodiments, the invention provides for the use of an infusion-patch as herein described to deliver Treprostinil, for treating pulmonary arterial hypertension.

In some embodiments, the anesthetic, analgesic or anti-inflammatory for use according to this aspect, may comprise a neurotoxin, which in some embodiments, is isolated from *Clostridium botulinum*.

DETAILED DESCRIPTION OF THE FIGURES

Detailed Description of the Invention

Figure 1B:
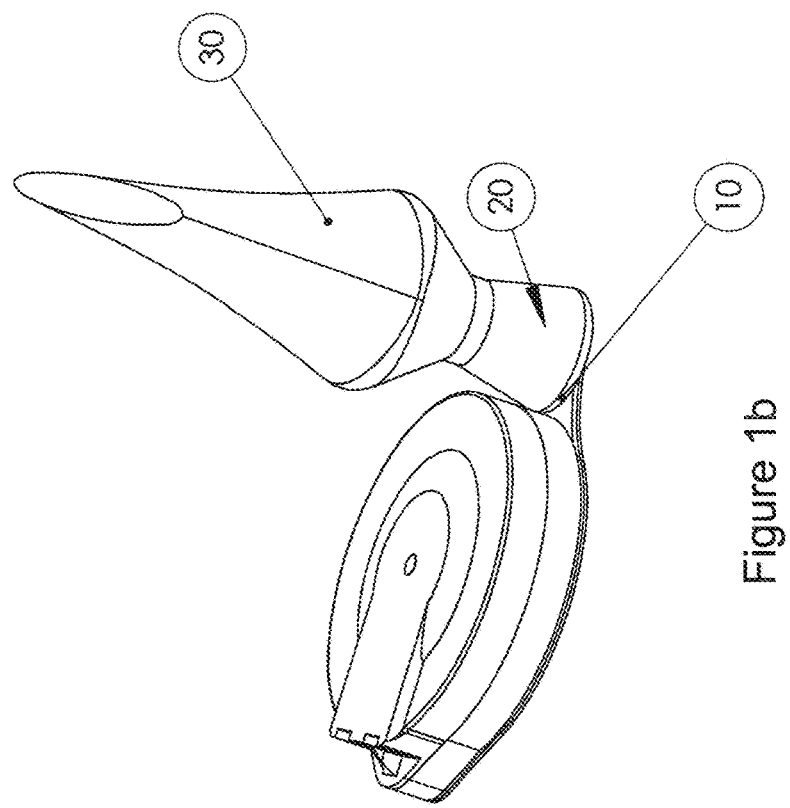
FIGS. 1a and 1b provide isometric views of a preferred embodiment of the infusion-patch of the current invention before and after connection of an anesthetic-reservoir, respectively.
Figure 1A:
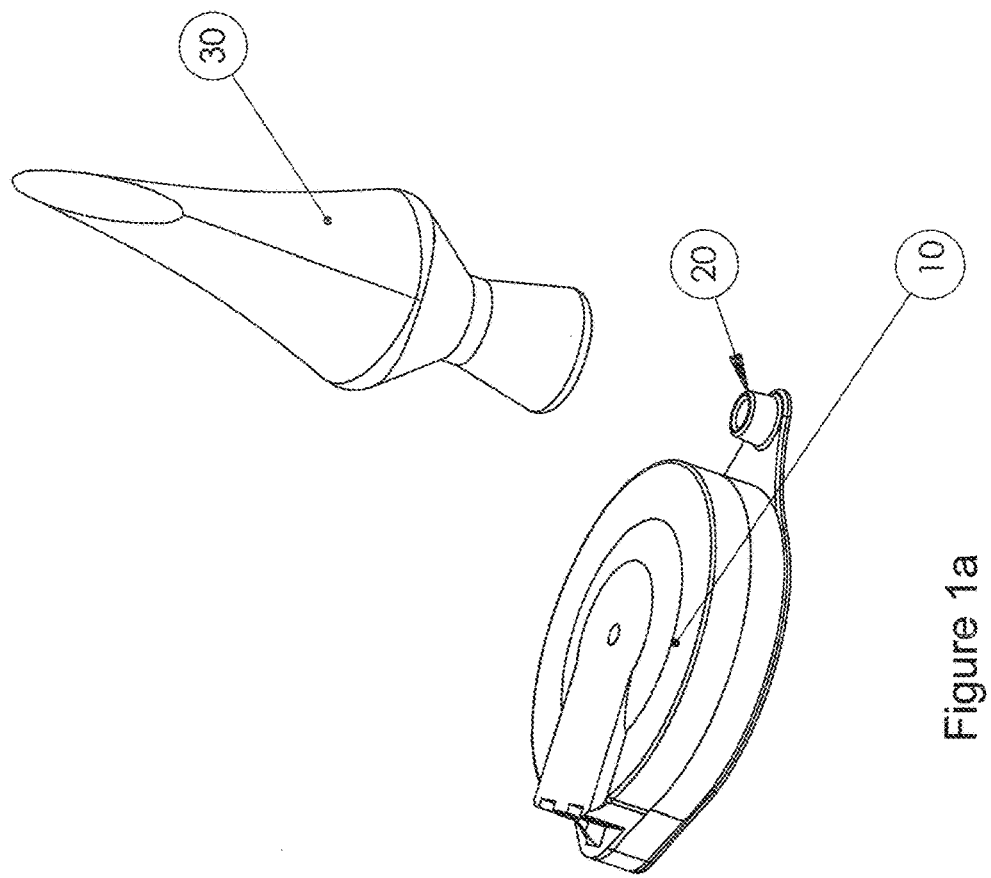

A preferred embodiment of the infusion-patch of the current invention is shown in FIG. 1a, showing the infusion-patch 10 and a connector 20 for attaching an anesthetic-reservoir 30. Said infusion-patch may be either an infusion-set or a patch-pump; the difference being that a patch-pump contains the drug to be delivered integrally within it, whereas an infusion set is connected via a tube to an external infusion pump which contains the drug. In both cases, the underside (not shown) of the infusion-patch contains a subcutaneous cannula which serves to deliver the drug into the subcutaneous fat layer under the dermis. The tube shown is a preferred embodiment of an external anesthetic reservoir 30. Said tube type reservoir is convenient for storing creams and lotions, and, advantageously, typically has a thread and screw-cap type closure arrangement, which is convenient for effecting a threaded connection to the connector 20 on the infusion-patch.

Referring now to FIG. 1b, the tube 30 which constitutes the anesthetic-reservoir in this embodiment, is shown connected to the infusion-patch 10; either by a threaded connection or by other means known in the art. Clearly any external reservoir could be used for this purpose, but, advantageously, the use of a tube provides for easy delivery of the anesthetic merely by squeezing said tube. Substances suitable for storing and using from said anesthetic-reservoir include any anesthetic, analgesic and/or anti-inflammatory drugs, including but not limited to, lidocaine or bupivacaine, salicylates, diclofenac, capsaicin, topical NSAIDs, antihistamines such as Mepyramine, topical steroids such as hydrocortisone, antipruritic agents and topical vasoconstrictive agents; either individually or in combination. Suitable formulations for such drugs or drug combinations include creams, foams and gels; for example Pluronic Lecithin Organogel (PLO Gel) which is commonly used for diclofenac administration.

Figure 2:
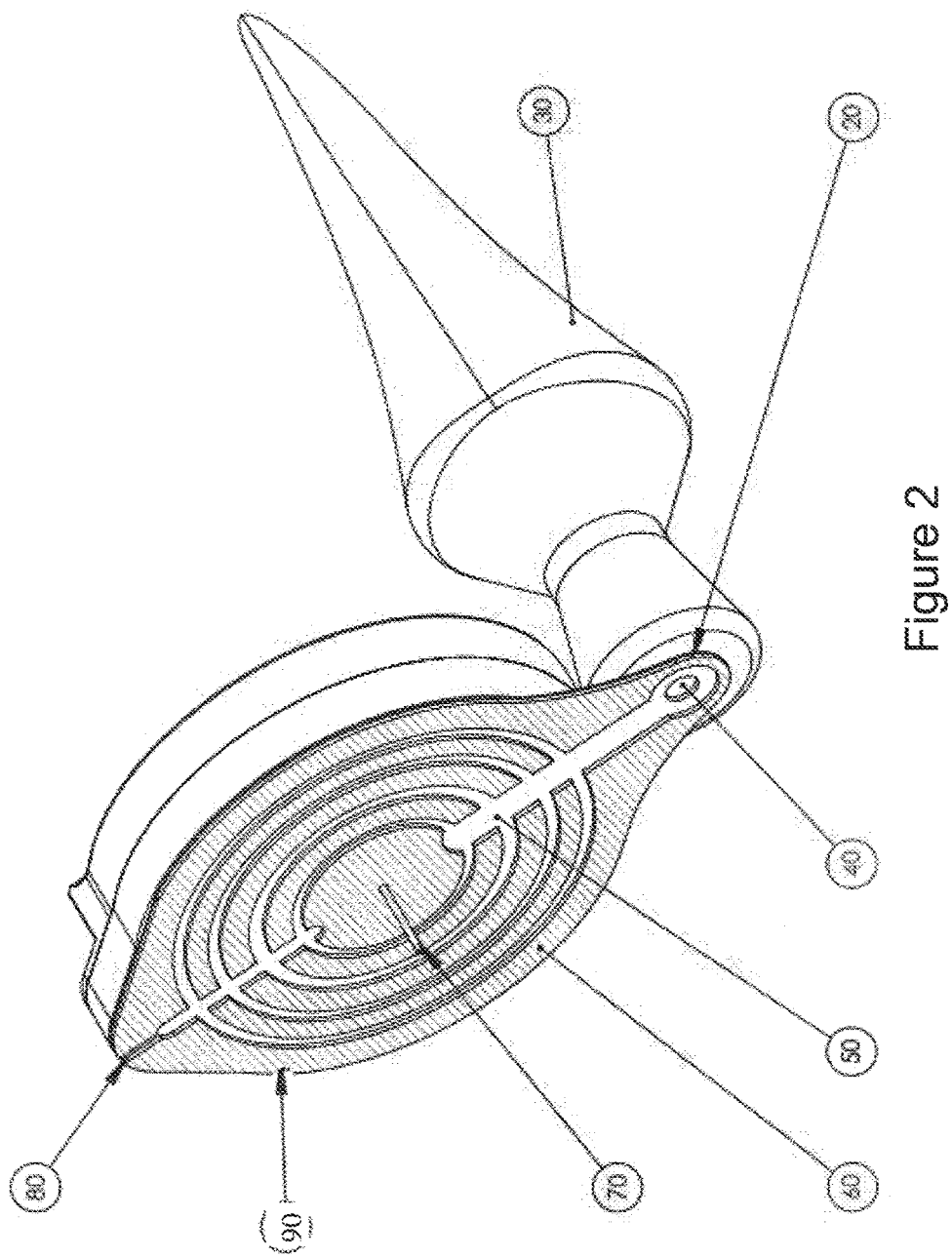
FIG. 2 provides an isometric view of said infusion-patch, showing a preferred embodiment of the structure of the skin-contact side of said patch.

Referring now to FIG. 2, the situation in which an external anesthetic-reservoir 30 (shown in this embodiment as a tube) is attached to the connector 20 is shown. In this configuration, there is a fluid connection established along a conduit 40 leading from the connector 20 to the skin-access areas 50 of the base 90 of the infusion-patch 10. Also shown in the base 90 are the adhesive areas 60 which serve to adhere the infusion-patch 10 to the skin and the cannula 70. There are a number of adhesives which typically serve this purpose, including those from 3M (MN, USA). In the preferred embodiment shown, the skin-access areas 40 have a channel structure such that they can lead the anesthetic along said skin-access areas such that said substance or excess thereof is eventually expelled from the base at one or more exit points 80.

The cannula 70 may be either a rigid or a flexible one, as it known in the art; the key point being that it serves to deliver a drug to the subcutaneous fat layer underneath the dermis.

Figure 3:
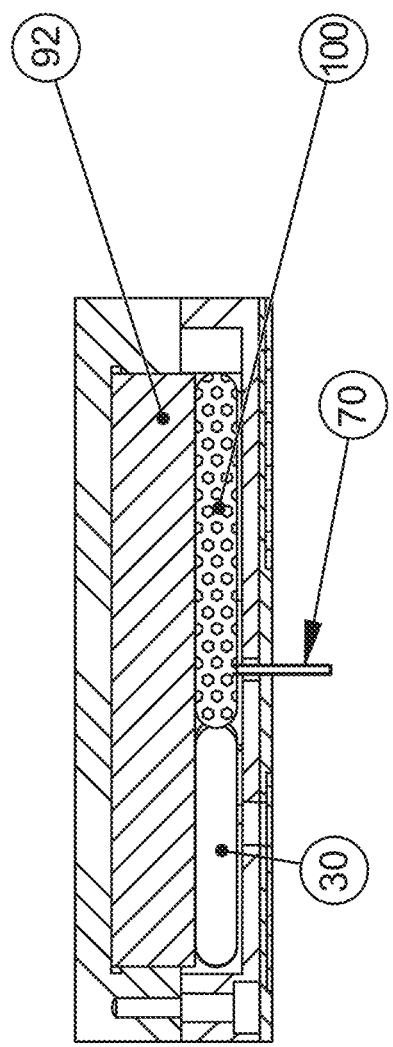
FIG. 3 provides a cross-sectional view of a further preferred embodiment of said infusion-patch, where the anesthetic-reservoir is integrated into the infusion-patch.

Referring now to FIG. 3, the case where the infusion-patch is a patch-pump is shown. In this preferred embodiment, an actuator 92 expands against an integral flexible drug-reservoir 100 containing the drug to be delivered. In use, the drug-reservoir 100 is in fluid connection with the cannula, such that the compression of said drug-reservoir causes the drug to be delivered. In the embodiment shown, said actuator 92 also compresses the anesthetic-reservoir 30 which is in fluid connection via the conduit (not shown) to the skin-access areas 50 in the base 90 of the pump.

Figure 4A:
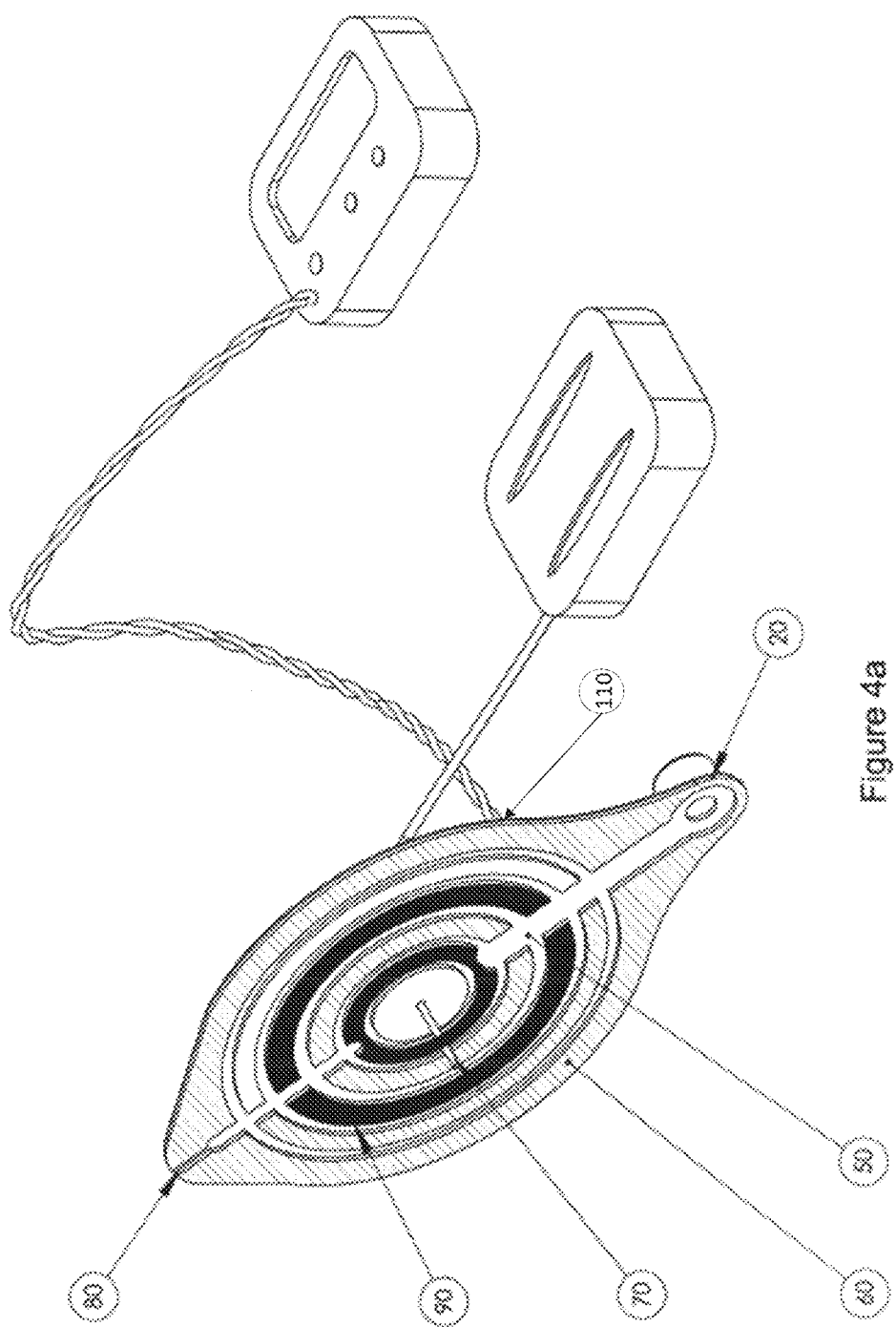
FIG. 4a provides an isometric view of a preferred embodiment of an enhanced infusion set integrating TENS electrodes in its underside.
Figure 4B:
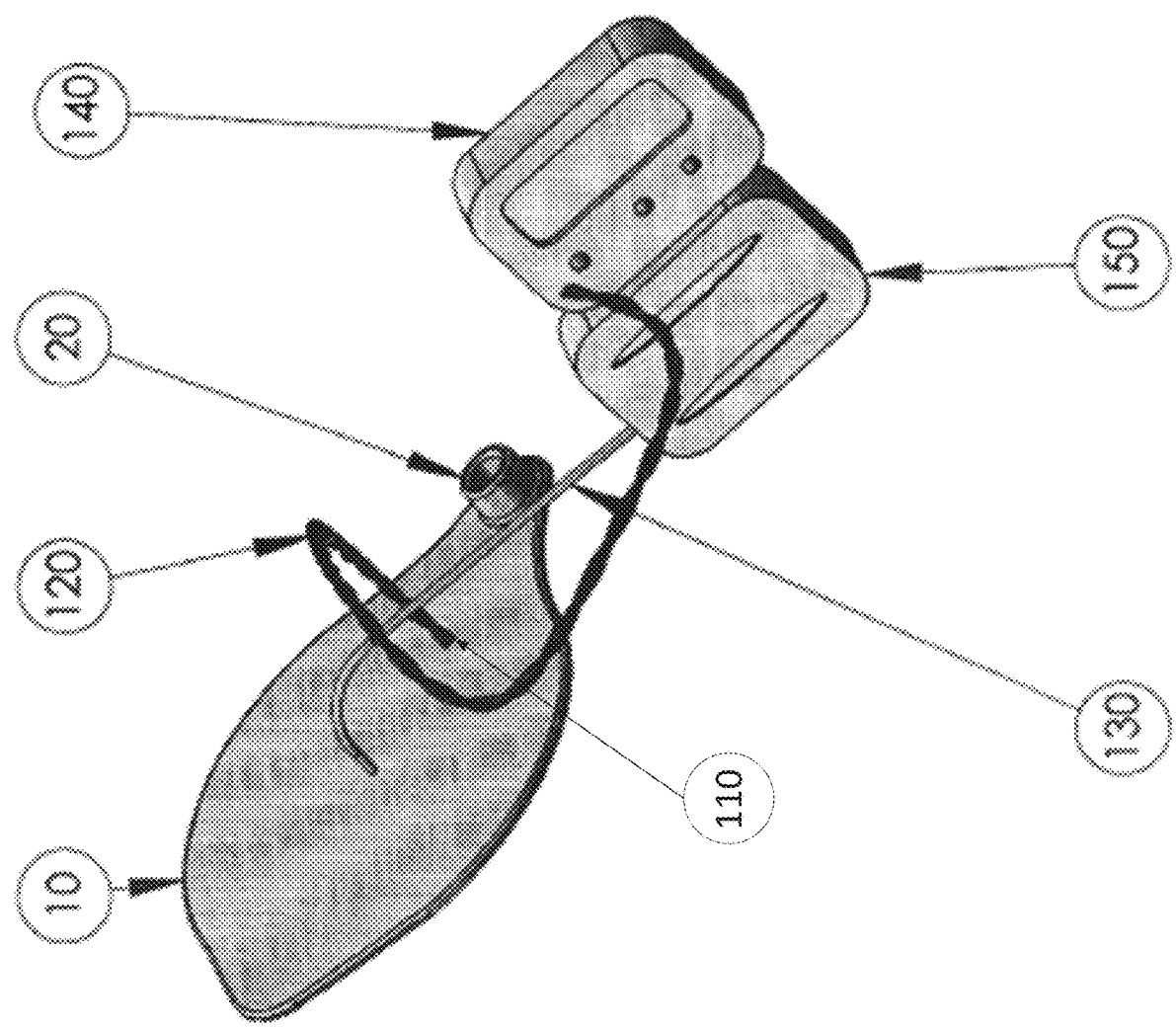
FIG. 4b provides an isometric view of the set of FIG. 4a, showing the connection of said set to an infusion set and TENS device.

Referring now to FIG. 4a, a preferred embodiment of an infusion set according to the present invention is shown. Looking at the base 90 of said infusion set, in addition to the skin-access areas 50 and the adhesive areas 60, a plurality of electrodes 110 are also provided in order to enable the use of TENS technology in order to further reduce the site pain. As shown in FIG. 4b, said electrodes 110 are connected by leads 120 to a TENS device 150, said device serving to Apply transcutaneous electrical nerve stimulation (TENS) to the skin area beneath the set; i.e. to use electric current to stimulate the nerves for therapeutic purposes. Also shown in FIG. 4b is the tube 30 leading from the infusion set to the infusion pump 140. For convenience it may be useful to bundle the TENS leads together with said tube. Additionally, even though the infusion pump 140 and TENS device 150 are shown here as separate units, an integrated pump/TENS unit would simplify the operation and is thereby included in the present invention.

As will be obvious to one skilled in the art, the present invention can be used in combination with one or more of the prior art pain-reduction techniques. For example, in addition to replenishing the drug in the skin-contact areas under the infusion-patch, the adhesive layer of said patch may also contain a pain-reducing drug. Additionally, the infusion site can be treated some days in advance using capsaicin and/or be rubbed with an anesthetic or anti-inflammatory cream directly before attaching the infusion-patch. Systemic pain-reduction and/or anti-inflammatory drugs may also be used in addition.

What is claimed is:

1. A method of administering a drug using an infusion-patch, the infusion-patch comprising a cannula, a base, an adhesive region in the base, a skin-access area within the base, a drug-reservoir integral to and within the infusion-patch, and a conduit within the skin-access area, wherein the infusion-patch is a patch-pump, the method comprising:
    attaching the base of the infusion-patch to a surface of a skin using the adhesive region;
    transferring an anesthetic substance from a first anesthetic-reservoir through the conduit to the skin-access area and to the surface of the skin;
    at least partially replenishing the anesthetic substance in the skin-access area without removing the infusion-patch from the surface of the skin; and
    delivering the drug from the drug-reservoir to the cannula, the cannula not being in fluid communication with the conduit.

2. The method of claim 1, wherein:
the infusion-patch further comprises an actuator, and
delivering the drug from the drug-reservoir to the cannula comprises using the actuator.

3. The method of claim 1, further comprising:
compressing the first anesthetic-reservoir to propel the anesthetic substance through the conduit.

4. The method of claim 1, further comprising:
applying transcutaneous electrical nerve stimulation to the skin.

5. The method of claim 1, further comprising:
treating the surface of the skin with an anesthetic or anti-inflammatory cream before attaching the base of the infusion-patch to the surface of the skin.

6. The method of claim 1, further comprising:
squeezing the first anesthetic-reservoir to deliver the anesthetic substance to the surface of the skin.

7. The method of claim 1, wherein the anesthetic substance is in a form selected from the group consisting of including creams, liquids, and foams.

8. The method of claim 7, wherein the anesthetic substance comprises a compound selected from the group consisting of anesthetics, analgesics, and anti-inflammatory substances.

9. The method of claim 7, wherein the anesthetic substance is a toxin isolated from *Clostridium botulinum*.

10. The method of claim 1, further comprising:
attaching the first anesthetic-reservoir to the infusion-patch.

11. The method of claim 10, wherein:
the infusion-patch comprises a connector,
attaching the first anesthetic-reservoir to the infusion-patch comprises attaching the first anesthetic-reservoir to the connector.

12. The method of claim 11, the method comprising:
detaching the first anesthetic-reservoir from the infusion-patch, and
attaching a second anesthetic-reservoir to the infusion-patch to the connector.

13. The method of claim 1, further comprising:
delivering the drug from the drug-reservoir to a subcutaneous fat layer underneath a dermis of the skin.

14. The method of claim 13, wherein:
the drug is Treprostinil.

15. The method of claim 14, wherein the anesthetic substance is a neurotoxin.

16. The method of claim 1, wherein:
the skin-access area is a channel in the base,
the channel comprises apertures located along a length of the channel,
the method further comprising:
releasing the anesthetic substance in the channel externally from the base.

17. The method of claim 16, wherein:
the apertures comprise an exit point,
the method further comprising:
expelling excess anesthetic substance from the base through the exit point.

18. The method of claim 17, wherein:
expelling excess anesthetic substance from the base through the exit point is in a direction different from a direction defined by a longitudinal axis along the cannula.

19. A method of administering a drug using an infusion-patch, the infusion-patch comprising a cannula, a base, an adhesive region in the base, a drug-reservoir integral to and within the infusion-patch, and a first anesthetic-reservoir, wherein the infusion-patch is a patch-pump, the method comprising:
attaching the base of the infusion-patch to a surface of a skin using the adhesive region;
delivering an anesthetic substance from the first anesthetic-reservoir to an aperture, wherein:
the base defines a channel,
the base defines the aperture along a length of the channel,
the first anesthetic-reservoir is in fluid communication with the channel and the aperture, and
the cannula is not in fluid communication with the channel;
contacting the anesthetic substance with the surface of the skin when the anesthetic substance is disposed in the aperture; and
at least partially replenishing the anesthetic substance in the aperture without removing the infusion-patch from the surface of the skin; and
delivering the drug from the drug-reservoir to the cannula for hours.

20. The method of claim 19, further comprising:
detaching the first anesthetic-reservoir from the base, and attaching a second anesthetic-reservoir to the base.

* * * * *